United States Patent [19] … [11] 4,088,465
Uda et al. … [45] May 9, 1978

[54] PROCESS FOR RECOVERING A COMBUSTIBLE GAS

[75] Inventors: Kazumi Uda, Fukuyama; Motohiko Tamura, Mihara; Ichiro Nishiura, Takehara; Hiroshi Fujiike, Mihara, all of Japan

[73] Assignee: Mitsubishi Jukogyo Kabushiki Kaisha, Tokyo, Japan

[21] Appl. No.: 746,625

[22] Filed: Dec. 1, 1976

Related U.S. Application Data

[63] Continuation-in-part of Ser. No. 732,075, Oct. 13, 1976, abandoned.

[30] Foreign Application Priority Data

Oct. 20, 1975 Japan ............................. 50-126105

[51] Int. Cl.² ................ B01D 53/30; F17C 13/02; G01N 25/54; G01N 33/22
[52] U.S. Cl. .................................. 62/54; 23/232 R; 23/232 E; 55/18; 55/212; 220/85 VR
[58] Field of Search ............. 23/232 E, 254 E, 255 E, 23/232 R; 55/18, 80, 212, 270; 137/2; 220/85 VR, 85 VS, 88 B; 62/54

[56] References Cited

U.S. PATENT DOCUMENTS

| | | |
|---|---|---|
| 1,510,433 | 9/1924 | Hosmer ............................. 55/80 X |
| 1,779,569 | 10/1930 | Thompson ....................... 23/232 E |
| 1,977,481 | 10/1934 | Jones ................................ 23/232 E |
| 2,049,987 | 8/1936 | Willenborg .................... 23/232 E X |
| 2,508,588 | 5/1950 | Waltman ....................... 23/232 R X |
| 2,585,882 | 2/1952 | Weissman et al. ............ 23/232 E X |
| 3,783,911 | 1/1974 | Husa et al. ................. 220/85 VR X |
| 3,886,759 | 6/1975 | McNamee .................. 220/85 VR X |

OTHER PUBLICATIONS

Perry, Chemical Engineers' Handbook, pp. 24-27, 24-88 thru 24-90, 4th Edition (1963).

Primary Examiner—Joseph Scovronek
Attorney, Agent, or Firm—Cushman, Darby & Cushman

[57] ABSTRACT

An improved process for recovering a combustible gas including a first means for measuring the relative concentration of combustible gas and combustion-supporting gas before the gaseous mixture enters a gas recovering apparatus, and a second means for determining the relative concentration of combustible gas and combustion-supporting gas after the gaseous mixture leaves the gas recovering apparatus. The first gas detecting means prevents a gaseous mixture containing a combustible gas in a concentration less than the U.E.L. from entering the gas recovering apparatus. The second detecting means controls the gas recovering apparatus to insure that the concentration of combustible gas never falls below the upper limit of the detonation range.

10 Claims, 3 Drawing Figures

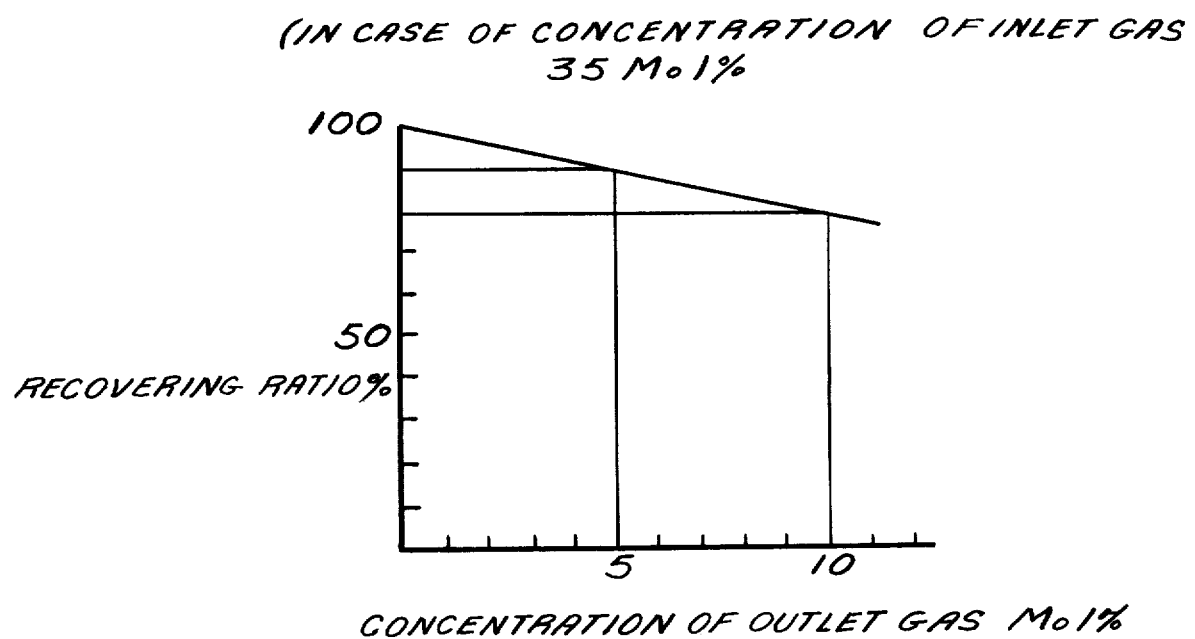

PROCESS FOR RECOVERING A COMBUSTIBLE GAS

CROSS-REFERENCE TO RELATED APPLICATION

This is a continuation-in-part of our co-pending U.S. patent application Ser. No. 732,075, filed Oct. 13, 1976, and now abandoned.

BACKGROUND OF THE INVENTION

The recovery of a combustible gas, for example gasoline vapor, from a mixture including air, requires a thorough consideration of the possibility of explosion and detonation. The present invention is intended to minimize the possibility of detonation when recovering a combustible gas.

In a mixture of a combustible gas (e.g. a hydrocarbon vapor such as gasoline vapor) and a combustion-supporting gas (e.g. air) it is important to consider the relative volume of each of the gases. For every such gaseous mixture there is a minimum and a maximum percentage of the combustible gas between which the composition must lie in order for an explosion to occur. If the concentration of the combustible gas is too high for an explosion to occur, the concentration of combustible gas is said to be in excess of the upper explosion limit (hereinafter referred to as U.E.L.). If the concentration of the combustible gas is too low to permit an explosion to occur, the concentration of combustible gas is said to be less than the lower explosion limit (hereinafter referred to as L.E.L.).

In a process for recovering a combustible gas it is uneconomical to add additional combustible gas to a mixture in order to obtain a concentration of the combustible gas at a value in excess of the U.E.L. Furthermore, it is not economical to dilute the concentration of a combustible gas to a value less than the L.E.L., since then the recovery process must treat too large a volume of gas. Nevertheless, it is dangerous to attempt to recover a combustible gas from a mixture containing a concentration of combustible gas above the L.E.L. and below the U.E.L.

The danger of explosion cannot be completely eliminated by taking those precautions which are well known in the art. Thus, for example, it is not feasible to eliminate all possibility of electrostatic discharge capable of igniting a gaseous mixture within the explosive limits. In addition, the possibility of accidental failure of equipment can never be completely eliminated.

If a mixture of a combustible gas and a combustion-supporting gas within the explosive limits is ignited, either an explosion or a detonation will follow. Apparatus designed to recover combustible gases generally incorporate safety valves and special plates which are designed to release the explosive pressure to the outside of the apparatus, thereby preventing complete destruction of the apparatus in the event of an explosion. However, the pressures generated by a detonation are much greater than the pressures generated by an explosion. As a result, it is not practical to design apparatus to recover combustible gases which can withstand the pressure of a detonation. Hence it is of particular importance to protect gas recovery apparatus from the extreme pressures generated by a detonation. Apparatus designed to recover a combustible gas may be damaged or totally destroyed by such a detonation.

A discussion of detonation theory is found in the *McGraw-Hill Encyclopedia of Science and Technology*, Volume 5, pages 145-53 (1966), which is hereby incorporated by reference. It may be noted that the range of mixtures of a combustible gas and a combustion-supporting gas which will produce a detonation is both narrower than and within the range of gaseous mixtures of the same substances which will produce an explosion. It is therefore possible to avoid a detonation by controlling the concentration of the components of a gaseous mixture composed of a combustible gas and a combustion-supporting gas. As those in the art are aware, however, present processes for recovering a combustible gas do not take into account the importance of controlling the relative concentrations of the components of the gaseous mixture.

SUMMARY OF THE INVENTION

The present invention provides a process for recovering a combustible gas including means for continuously measuring the relative concentrations of the components of the gaseous mixture.

It is an object of the present invention to provide a process for recovering a combustible gas which prevents a gaseous mixture capable of explosion from entering the gas recovering apparatus.

It is another object of the present invention to provide a process for recovering a combustible gas which prevents a gaseous mixture capable of detonation from entering the gas recovering apparatus.

It is a further object of the present invention to provide a process for recovering a combustible gas which prevents a gaseous mixture capable of detonation from forming within the gas recovering apparatus.

It is a further object of the present invention to provide a process for recovering a combustible gas which protects the gas recovering apparatus from damage by detonation.

Yet another object of the present invention is to provide a process for recovering a combustible gas which is economical to operate.

Surprisingly, it has been found that by determining the relative concentrations of the components of a gaseous mixture composed of a combustible gas and a combustion-supporting gas before it enters the gas recovering apparatus, and as it leaves the gas recovering apparatus, it is possible to achieve the objects of the present invention.

2 is a gas recovering apparatus;

3 is a means for measuring the relative concentrations of the components of the gaseous mixture before they enter the gas recovering apparatus;

4 is a means for measuring the relative concentrations of the components of the gaseous mixture as they leave the gas recovering apparatus;

5 and 6 are transfer pipes; and 7 and 8 are discharge pipes.

Figure 2:
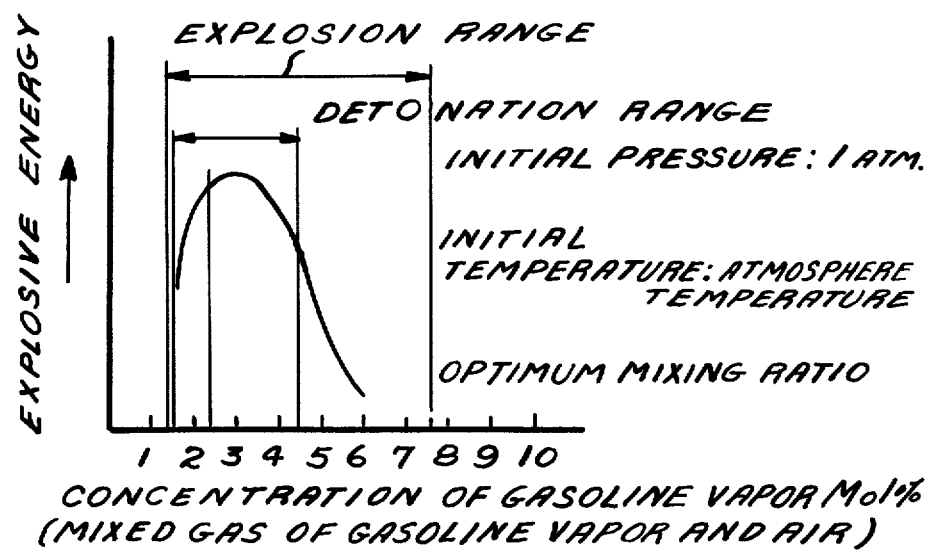

FIG. 2 shows the explosive energy of a mixture of gasoline vapor and air, as a function of the relative concentrations of the components of the gaseous mixture. The detonation range and the explosion range as a function of the relative concentrations of the components of the gaseous mixture are also shown.

FIG. 3 shows the recovery ratio of a combustible gas in a process according to the present invention as a function of the concentration of combustible gas leaving the gas recovering apparatus.

DETAILED DESCRIPTION OF THE INVENTION

In accordance with the present invention an improved process for recovering a combustible gas is provided by means to determine the relative concentrations of the components of a gaseous mixture composed of a combustible gas and a combustion-supporting gas, both before the gaseous mixture enters the gas recovery apparatus and after the gaseous mixture leaves the gas recovering apparatus. Means for determining the relative concentrations of combustible gas and combustion-supporting gas are well known to those skilled in the art. Suitable gas densitometers (devices for determining the relative concentration of combustible gas and combustion-supporting gas) are:

| Manufacturer | Form | Model | Address |
|---|---|---|---|
| Riken Keiki KK | Contact-combusion form | GP 830-2D5 | 2-7-6 Azukizawa Itabashi-ku, Tokyo |
| Riken Keiki KK | Light wave interference form | 762 | 2-8-6 Azukizawa Itabashi-ku, Tokyo |
| KK Horiba Seisakusho KK | Infrared absorption form NDIR | BIA-IA | 2 Shiba Nishikubo-Sakuragawa-cho Minato-ku, Tokyo |
| Yanagimoto Seisakusho | Hydrogen flame ionization detecting form FID | — | 28 Shimotoba Joshunga-mae-machi, Fushimi-ku, Kyoto |
| MSA Hokushin KK* | Thermal conductivity | — | 3-30-1 Shimomaruko, Ota-ku, Tokyo |
| Komyo Rikagaku Kogyo KK | Thermal conductivity | FTC-1 | 1-8-24 Chuo-cho Meguro-ku, Tokyo |

*MSA Hokushin KK is a joint venture of Mine Safety Appliance Co., Ltd. of U.S.A. and Hokushin Denki Seisakusho of Japan (manufacturer of gas denistometers).

Other means of detection will be well known to those in the art.

In accordance with the present invention, the relative concentrations of the combustible gas and combustion-supporting gas are determined before the gas to be treated enters the gas recovering apparatus. Only gaseous mixtures containing a concentration of combustible gas above the U.E.L. are permitted to enter the gas recovering apparatus. Gaseous mixtures containing a concentration of combustible gas below the U.E.L. are not treated in accordance with the process of the present invention.

In accordance with the present invention it has been found desirable not to treat gaseous mixtures containing a concentration of combustible gas below the U.E.L. The first reason for not treating such mixtures is to insure the safety of the gas recovering apparatus and the personnel who operate it. As explained above, so long as the concentration of the combustible gas is above the U.E.L. it is not possible for a detonation to occur within the gas recovering apparatus. A second reason for not treating gaseous mixtures containing a concentration of combustible gas below the U.E.L. is of importance when the concentration of combustible gas is so low that it is also below the L.E.L. In the latter case, where the concentration of combustible gas is below the L.E.L., the efficiency of recovering combustible gas is poor and it is therefore uneconomical to attempt to recover a combustible gas from such a gaseous mixture.

As described above, the first means for detecting the relative concentrations of the components of the gaseous mixture permits only mixtures containing a combustible gas concentration above the U.E.L. to enter the gas recovering apparatus. A typical gas recovering apparatus is described in applicants' copending application, Ser. No. 732,074, filed Oct. 13, 1976 and now abandoned, which is hereby incorporated by reference. Treatment of the gaseous mixture of a combustible gas and a combustion-supporting gas to recover the combustible gas naturally lowers the concentration of combustible gas in the gas recovering apparatus. It is for this reason that a second means for measuring the concentration of combustible gas is provided to test the gaseous mixture as it leaves the gas recovering apparatus. It is the purpose of this second means for determining the concentration of combustible gas to insure that the combustible gas leaving the gas recovering apparatus does not fall within the detonation range, i.e., the range of composition of the gaseous mixture in which detonation may occur. As described above, and as may be seen from FIG. 2, the detonation range is both narrower and within the explosion range for a mixture of a combustible gas and a combustion-supporting gas. The precise manner in which the second means for determining the exit gas composition, i.e., the composition of the gaseous mixture leaving the gas recovering apparatus, prevents the exit gas composition from falling within the detonation range will depend on the operation of the gas recovering apparatus. For example, if the gas recovering apparatus effects the recovery of a combustible gas by a cycle of compression, cooling, and condensation, the means for measuring the composition of the exit gas can be arranged to prevent the exit gas from falling within the detonation range by controlling either the operating pressure or the cooling temperature. The precise manner in which these parameters are adjusted to prevent the exit gas from falling within the detonation range will depend upon the components of the gaseous mixture. Once the identity of each of the components of the gaseous mixture, i.e., the identity of the combustible gas and the identity of the combustion-supporting gas, is known, the detonation range for that particular gaseous mixture can readily be determined. Given that information, one of ordinary skill in the art can easily arrange the means for determining the exit gas composition so as to prevent the exit gas composition from falling within the detonation range. As explained above, the first and second means for measuring the concentration of combustible gas tests the gaseous mixture as it enters and leaves the gas recovering apparatus. The first and second means for measuring the concentration of combustible gas may be gas densitometers of the various types listed above. In performing the process of the present invention it is not absolutely necessary to separately install one gas densitometer to measure the concentration of combustible gas as it enters the gas recovering apparatus and another gas densitometer to measure the concentration of combustible gas as it leaves the gas recovering apparatus. Instead, it is possible to periodically shift a single gas densitometer from the entrance to the exit of the gas recovering apparatus, and vice versa, in measuring the concentration of combustible gas and controlling the operation of the gas recovering apparatus accordingly.

The foregoing discussion may be clarified by reference to a particular example, viz. the recovery of gasoline vapor. Gasoline vapor at an oil storage facility or oil refinery is generally found to contain from about 10% to 35% by volume combustible gas (gasoline vapor). The explosion and detonation ranges of gasoline vapor are generally as follows:

Upper limit of the explosion range: 7.6% by volume
Upper limit of the detonation range: 4.5% by volume
Lower limit of the detonation range: 1.6% by volume
Lower limit of the explosion range: 1.4% by volume In the process of the present invention, gasoline vapor having a concentration within the range of about 10% to about 35% by volume is introduced into the gas recovering apparatus and treated so that the concentration of combustible gas (gasoline vapor) is gradually lowered. Using the process of the present invention, the gas recovering apparatus is controlled so that the exit gas composition is about 5% by volume combustible gas (gasoline vapor), which is of course in excess of the upper limit of the concentration of the detonation range. Thus, if by accident the gasoline vapor should ignite and explode for some reason, the explosive energy is relatively small. It is within the skill of the art to construct a gas recovering apparatus which can withstand such explosive pressure. From the standpoint of economic operation of a gas recovering apparatus, if the entrance concentration of gasoline vapor is 35% by volume and the exit concentration of gasoline vapor is 5% by volume, the recovery ratio approaches 90% by volume which is very favorable. The operation of the gas recovering process of the present invention is particularly favorable when it is remembered that all risk of detonation is removed by means of the present process. In this regard, it must be remembered that when in prior art processes the combustible gas fell within the detonation range, and then by accident ignited and detonated, it emitted a huge explosive force in a short time, which inevitably destroyed the gas recovering apparatus. Since the process of the present invention overcomes this serious difficulty of the prior art, the present process is inherently more economical to operate. Thus, from the viewpoints of both safety and economy, the exit gas composition of gasoline vapor exiting from a gas recovering apparatus operated according to the process of the present invention is 5% by volume, which is a little higher than the upper limit of the detonation range.

By using the improved process of the present invention all possibility of detonation within the gas recovering apparatus is eliminated. Furthermore, to the extent that the gaseous mixture contains a concentration of combustible gas above the U.E.L. the danger of explosion within the gas recovering apparatus is substantially reduced. During the operation of the gas recovering apparatus the concentration of the combustible gas may fall below the U.E.L. although it will always remain above the detonation range. Thus there is still some possibility of an ordinary explosion occurring within the gas recovering apparatus. However, it is within the skill of the art to construct gas recovering apparatus which will withstand the pressure of an ordinary explosion, i.e. an explosion which does not become a detonation. As those in the art are aware, the explosive pressure of an ordinary explosion of a mixture of, for example, a hydrocarbon vapor and air mixed in the optimum mixing ratio is about 7 or 8 times the initial pressure. The optimum mixing ratio, also called the stoichiometric composition, is the composition of a mixture of a combustible gas and a combustion-supporting gas which will theoretically burn completely consuming all of the combustible gas and all of the combustion-supporting gas originally present. In contrast to the ordinary explosive pressure of seven or eight times the initial pressure, the pressure of a detonation may be 20 times the initial pressure or more. Detonation pressures in the region of 20,000 atmospheres are known. *McGraw-Hill Encyclopedia of Science and Technology*, supra.

Detonation of any particular combustible gas is affected by both the pressure and temperature of the combustible gas, the size and shape and condition of the interior walls of the container of the combustible gas, and possibly other factors. It is therefore difficult to precisely define a detonation range for any particular combustible gas. However, it may be said with certainty that a detonation range is a very narrow, limited concentration range centering around the theoretically optimum mixing ratio for combustion, within the upper and lower explosive limits of the combustible gas. The following detonation ranges are to be taken as approximate in view of the factors mentioned above, and were determined at atmospheric pressure and normal temperature for a mixture of air and the combustible gas mentioned.

| Combustible Gas | Detonation Range (Concentration of Combustible Gas by Volume) |
|---|---|
| Gasoline vapor | 1.6 – 4.5% |
| Propane vapor | 2.2 14 9.2% |
| Butadiene vapor | 3.0 – 6.0% |

Figure 1:
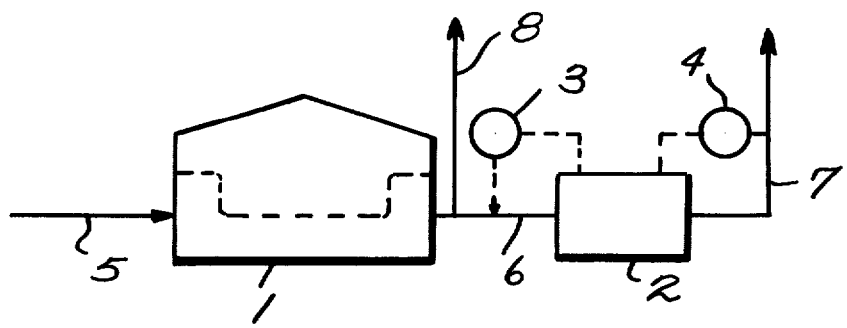
FIG. 1 is a flow sheet showing one embodiment of the process of the present invention. In this Figure, 1 is a container for a gaseous mixture of a combustible gas and a combustion-supporting gas.

The improved process for recovering a combustible gas may be illustrated with respect to the drawings. FIG. 1 is a flow sheet showing one embodiment of practicing the improved process of the present invention. In FIG. 1 a gaseous mixture composed of a combustible gas and a combustion-supporting gas is collected by pipe 5 and stored in a holding tank 1. Thereafter, the gaseous mixture is sent to a gas recovering apparatus 2 by feed piping 6. The composition of the gaseous mixture moving from holding tank 1 to the gas recovering apparatus 2 is tested by the first detecting means 3. The first detecting means 3 permits the gaseous mixture to enter the gas recovering apparatus only if the concentration of a combustible gas is above the U.E.L.

The gaseous mixture leaving the gas recovering apparatus is monitored by a second detecting means. The second detecting means controls the operation of the gas recovering apparatus so that the gaseous mixture leaving the gas recovering apparatus contains sufficient combustible gas to remain above the detonation range. The second gas detecting means is denoted at 4. The gas leaving the gas recovering apparatus 2 is discharged through piping 7.

FIG. 2 illustrates the relationship of explosive energy to the relative composition of a gaseous mixture composed of gasoline vapor and air. The detonation range and explosion range for a mixture of gasoline vapor and air are illustrated, as is the optimum mixing ratio. The concentration of gasoline vapor is given in units of mol percent. Normal atmospheric temperature and pressure are assumed as the intitial temperature and pressure.

FIG. 3 illustrates the relation between the concentration of a combustible gas in the gaseous mixture leaving the gas recovering apparatus and the efficiency of the process for recovering a combustible gas, when the initial concentration of combustible gas in the gaseous mixture entering the gas recovering apparatus is 35 mol %. It will be seen from FIG. 3 that when the gaseous mixture entering the gas recovering apparatus contains 35 mol % of a combustible gas, and the combustible gas is recovered until the concentration reaches the upper limit of the detonation range, for example 5 mol %, the recovering ratio is 90%.

Specific examples of the present invention in a gasoline vapor recovering apparatus will be explained hereinbelow.

EXAMPLE 1

The concentration of a gasoline vapor was measured at 10% by volume at the entrance of a gasoline vapor recovering apparatus, measured by a hydrocarbon densitometer, which was a little higher than the U.E.L. of 7.6% by volume. The gasoline vapor recovering apparatus was so adapted that it was driven when the concentration at the entrance was at least 10% by volume, and it was not driven and the gasoline vapor was released per se into the atmosphere via a discharge pipe (8 of FIG. 1) when the concentration at the entrance was less than 10% by volume. The gasoline vapor recovering apparatus was at first driven, when the gasoline vapor concentration at the entrance was more than 10% by volume, however, because the concentration of gasoline vapor at the entrance lowered to less than 10% by volume, the apparatus was stopped and the gasoline vapor was released per se into the atmosphere.

EXAMPLE 2

The concentration of a gasoline vapor was measured at 5% by volume at the exit of a gasoline vapor recovering apparatus, measured by a hydrocarbon densitometer, which was higher than the upper limit of the detonation range of 4.4% by volume. The apparatus was driven. When the concentration of hydrocarbon at the exit lowered to less than 5% by volume, the operating pressure of the recovering apparatus was reduced, the operating temperature was raised and/or the flowing amount of an absorbent was decreased. In short, the operating conditions were varied in a manner known to those of ordinary skill in the art in order to raise the gasoline vapor concentration at the exit.

EXAMPLE 3

This is a specific example of varying the operating conditions in order to raise the gasoline vapor concentration at the exit. The values vary depending upon the form of the recovering apparatus, but an actual example in the case of an apparatus used by the applicants will be shown.

| Concentration at the exit | 3% by volume | → | 5% by volume |
|---|---|---|---|
| Operating pressure | 1.8 kg/cm$^2$G | → | 1.6 kg/cm$^2$G |
| Operating temperature | 2° C | → | 5° C |
| Flowing amount of the absorbent | 10 m$^3$/H | → | 7 m$^3$/H |

The foregoing is an example of varying all of the pressure, temperature and amount of the absorbent. However, depending upon conditions, the variable(s) to be adjusted may be freely selected, such as only varying the pressure.

It is understood that various other modifications will be apparent to and can readily be made by those skilled in the art without departing from the scope and spirit of this invention. Accordingly, it is not intended that the scope of the claims appended hereto be limited to the description set forth, but rather that the claims be construed as encompassing all the features which reside in the present invention including all features which would be treated as equivalents thereof by those skilled in the art to which this invention pertains.

What is claimed is:

1. In a process for recovering a combustible gas in a gas recovering apparatus from a gaseous mixture comprising a combustible gas and a combustion-supporting gas, said gaseous mixture having a known explosion range upper limit and a known detonation range upper limit, the improvement comprising:

measuring an initial combustible gas content of said gaseous mixture before said gaseous mixture enters said gas recovering apparatus, permitting only gaseous mixtures having a combustible gas content above the explosion range upper limit to enter the gas recovery apparatus, recovering combustible gas from said gaseous mixture to reduce the combustible gas content of said gaseous mixture below the explosion range upper limit but above said detonation range upper limit, measuring a final combustible gas content of said gaseous mixture as said gaseous mixture leaves said gas recovering apparatus, and maintaining said combustible gas content in said gas recovery apparatus above said detonation range upper limit.

2. The process of claim 1 wherein said combustible gas is gasoline vapor and said combustion-supporting gas is air.

3. The process of claim 1 wherein said combustible gas is propane vapor and said combustion-supporting gas is air.

4. The process of claim 1 wherein said combustible gas is butadiene vapor and said combustion-supporting gas is air.

5. The process of claim 1 wherein said combustible gas is a hydrocarbon and said combustion-supporting gas is air.

6. The process of claim 1 wherein said combustible gas is recovered by a process of compression, cooling, and condensation.

7. The process of claim 2 wherein the final combustible gas content of said gaseous mixture is 5% by volume.

8. The process of claim 3 wherein the final combustible gas content of said gaseous mixture is 10% by volume.

9. The process of claim 4 wherein the final combustible gas content of said gaseous mixture is 7% by volume.

10. The process of claim 2 where the initial gasoline vapor content of the gaseous mixture is 35% by volume and the final gasoline vapor content of the gaseous mixture is 5% by volume.

* * * * *